United States Patent [19]

Lipsky et al.

[11] Patent Number: 5,047,401

[45] Date of Patent: Sep. 10, 1991

[54] USE OF DIPEPTIDE ALKYL ESTERS TO TREAT GVHD

[75] Inventors: Peter E. Lipsky; Dwain L. Thiele, both of Dallas, Tex.

[73] Assignee: Board of Regents, The University of Texas System, Austin, Tex.

[21] Appl. No.: 168,177

[22] Filed: Mar. 15, 1988

Related U.S. Application Data

[63] Continuation of Ser. No. 774,051, Sep. 5, 1985, Pat. No. 4,752,602.

[51] Int. Cl.$^5$ .............................................. A61K 37/02
[52] U.S. Cl. ..................................................... 514/19
[58] Field of Search ........................ 530/334; 560/41; 514/19

[56] References Cited

U.S. PATENT DOCUMENTS 4,555,502  11/1985  Patchett et al. .
4,585,757  4/1986  Pang et al. .
4,616,012  10/1986  Neustadt et al. .

OTHER PUBLICATIONS

Nitecki et al., "A Simple Route to Sterically Pure Diketopiperazines", *J. of Organic Chem.*, 1967.

Ueda et al., "Facile Synthesis of Cyclic Dipeptides & Detection of Racemization", *Bull. Chem. Soc. of Japan*, 1983.

Goldman et al., Dipeptide Hydrolysis Within Intact Lysosomes in Vitro, North Holland Publishing Company–Amsterdam, vol. 33, No. 2, pp. 208–212.

Reeves et al., Accumulation of Amino Acids by Lysosomes Incubated with Amino Acid Methyl Esters*, The Journal of Biological Chemistry, vol. 254, No. 18, pp. 8914–8921.

Thiele et al., Phenotype of the Accessory Cell Necessary for Mitogen-Stimulated T and B Cell Response in Human Peripheral Blood: Delineation by its Sensitivity to the Lysosomotropic Agent, L-Leucine Methyl Ester, The Journal of Immunology, vol. 13, No. 5, Nov. 1983, pp. 2282–2290.

Verhoef et al., Inhibition of Human Natural Killer Activity by Lysosomotropic Agents, The Journal of Immunology, vol. 131, No. 1, Jul. 1983, pp. 125–131.

Shau et al., Depletion of NK Cells with the Lysosomotropic Agent L-Leucine Methy Ester and the In Vitro Generation of NK Activity from NK Precursor Cells, the Journal of Immunology, vol. 134, No. 2, Feb. 1985, pp. 1136–1141.

(List continued on next page.)

*Primary Examiner*—Johnnie R. Brown
*Assistant Examiner*—Stephen B. Maebius
*Attorney, Agent, or Firm*—Arnold, White & Durkee

[57] ABSTRACT

An alkyl ester of dipeptide consisting essentially of natural or synthetic L-amino acids with hydrophobic side chains. Preferable amino acids are leucine, phenylalanine valine, isoleucine, alanine, proline, glycine or aspartic acid beta methyl ester. Preferable dipeptides are L-leucyl L-leucine, L-leucyl L-phenylalanine, L-valyl L-phenylalanine, L-leucyl L-isoleucine, L-phenylalanyl L-phenylalanine, L-valyl L-leucine, L-leucyl L-alanine, L-valyl L-valine, L-phenylalanyl L-leucine, L-leucine, L-prolyl L-leucine, L-leucyl, L-valine, L-phenylalanyl L-valine, L-glycyl L-leucine, L-leucyl L-glycine or L-aspartyl beta methyl ester L-phenylalanine. Most preferable dipeptides are L-leucyl L-leucine, L-leucyl L-phenylalanine, L-valyl L-phenylalanine, L-phenylalanyl L-leucine, L-leucyl L-isoleucine L-phenylalanyl L-phenylalanine and L-valyl L-leucine.

The alkyl ester of the dipeptide is most preferably a methyl ester and may also be an ethyl ester or alkyl of up to about four carbon atoms such as propyl, isopropyl, butyl or isobutyl.

These alkyl esters of dipeptides consisting essentially of amino acids with hydrophobic side chains may be used to deplete cytotoxic T-lymphocytes or natural killer cells from organisms, cell populations or tissues.

6 Claims, 7 Drawing Sheets

OTHER PUBLICATIONS

Trinchieri et al., Anti-Viral Activity Induced by Culturing Lymphocytes with Tumor-Derived Or Virus-Transformed Cells, The Rockefeller University Press, 0022-1007/78/0501-1314, pp. 1314-1333.

Charley et al., Prevention of Lethal Murine Graft Versus Hose Disease by Treatment of Donor Cells with L-Leucyl-1-Leucine Methyl Ester, The American Society for Clinical Investigation, Inc., vol. 78, Nov. 1986, pp. 1415-1420.

Thiele et al., Lethal Graft-VS-Host Disease Across Major Histocompatibility Barriers: Requirement for Leucyl-Leucine Methyl Ester Sensitive Cytotoxic T Cells, The Journal of Immunology, vol. 138, No. 1, Jan. 1, 1987, pp. 51-57.

Gidlund et al., Enhanced NK Cell Activity in Mice Injected with Interferon and Interferon Inducers, Nature, vol. 273, Jun. 29, 1978, pp. 759-761.

Lopez et al., Association Between Pre-Transplant Natural Kill and Graft-Versus-Host Disease After Stem-Cell Transplantation, The Lancet, Nov. 24, 1978, pp. 1103-1106.

Seeley et al., Studies on Cytotoxicity Generated In Human Mixed Lymphocyte Cultures, The Journal of Immunology, vol. 123, No. 3, Sep. 1979, pp. 1303-1311.

Roder et al., Target-Effector Interaction in the Natural Killer Cell System, The Journal of Immunology, vol. 123, No. 6, Dec. 1979, pp. 2785-2790.

Kendall et al., The Dual Effect of Prostaglandin ($PGE_2$) and Ethanol on the Natural Killer Cytolytic Process: Effector Activation and NK-Cell-Target Cell Conjugate Lytic Inhibition, The Journal of Immunology, vol. 125, No. 6, Dec. 1980, pp. 2770-2777.

Lopez et al., Natural Killer Cells in Bone Marrow Transplantation, The Lancet, Nov. 8, 1980, p. 1025.

Breard et al., A Monoclonal Antibody Reactive with Human Peripheral Blood Monocytes, The Journal of Immunology, vol. 124, No. 4, Apr. 1980, pp. 1943-1948.

Zarling et al., Phenotypes of Human Natural Killer Cell Populations Detected with Monoclonal Antibodies, The Journal of Immunology, vol. 127, No. 6, Dec. 1981, pp. 2575-2580.

Ortaldo et al., Determination of Surface Antigens on Highly Purified Human NK Cells by Flow Cytometry with Monoclonal Antibodies, The Journal of Immunology, vol. 127, No. 6, Dec. 1981, pp. 2401-2409.

Timonen et al., Characteristics of Human Large Granular Lymphocytes and Relationship to Natural Killer and K Cells, J. Exp. Med. The Rockefeller University Press, vol. 153, Mar. 1981, pp. 569-582.

Reeves et al., Intracellular Disruption of Rat Heart Lysosomes by Leucine Methyl Ester: Effects on Protein Degradation, Proc. Natl. Acad. Sci. U.S.A., vol. 78, No. 7, pp. 4426-4429.

Herberman et al., Natural Killer Cells: Their Role in Defenses Against Disease, Science 214, 24, 1981.

Dokhelar et al., Natural Killer Cell Activity in Human Bone Marrow Recipients, Transplantation, vol. 31, No. 1, pp. 61-65.

Grimm et al., Lymphokine-Activated Killer Cell Phenomenon, Journal of Experimental Medicine, vol. 155, Jun. 1982, pp. 1823-1841.

Warner et al., Effects of a Cloned Cell Line with NK Activity on Bone Marrow Transplants, Tumour Development and Metastasis In Vivo, Nature, vol. 300, pp. 31-34.

Hiserodt et al., Differential Effects of Various Pharmacologic Agents on the Cytolytic Reaction Mechanism of the Human Natural Killer Lymphocyte: Further Resolution of Programming for Lysis and Kcil into Discrete Stages, The Journal of Immunology, vol. 129, No. 5, Nov. 1982, pp. 2266-2270.

Quan et al., Studies on the Mechanism of NK Cell Lysis, The Journal of Immunology, vol. 128, No. 4, Apr. 1982, pp. 1786-1791.

Seaman et al., Suppression of Natural Killing in Vitro by Monocytes and Polymorphonuclear Leukocytes, The Journal of Clinical Investigation, vol. 69, Apr. 1982, pp. 876-888.

Dempsey et al., The Differential Effects of Human Leukocytic Pyrogen/Lymphocyte-Activating Factor, T Cell Growth Factor, and Interferon on Human Natural Killer Activity, The Journal of Immunology, vol. 129, No. 6, Dec. 1982, pp. 2504-2510.

Koren et al., Modulation of Human NK Cells by Interferon and Prostaglandin $E_2$, Molecular Immunology, vol. 19, No. 10, pp. 1341-1346.

Katz et al., Mechanisms of Human Cell-Mediated Cytotoxicity, The Journal of Immunology, vol. 129, No. 1, Jul. 1982, pp. 287-296.

OTHER PUBLICATIONS

Hiserodt et al., Characterization of the Cytolytic Reaction Mechanism of the Human Natural Killer (NK) Lymphocyte: Resolution into Binding, Programming, and Killer Cell-Independent Steps, The Journal of Immunology, vol. 129, No. 4, Oct. 1982, pp. 1782–1787.

Bonavida et al., Molecular Interactions in T-Cell-Mediated Cytotoxicity, Immunological Rev., vol. 72, pp. 119–141.

Podack et al., Assembly of Two Types of Tubules with Putative Cytolytic Function by Cloned Natural Killer Cells, Nature, vol. 302, Mar. 31, 1983, pp. 442–445.

Dennert et al., Cytolysis by H-2-Specific T Killer Cells, J. Exp. Med. The Rockefeller University Press, vol. 157, May 1983, pp. 1483–1495.

Burns et al., Human Natural Killer Cells, Activated Lymphocyte Killer Cells, and Monocytes Possess Similar Cytotoxic Mechanisms, Proc. Natl. Acad. Sci. U.S.A., vol. 80, Dec. 1983, pp. 7606–7610.

Hattori et al., Inhibition of Human Natural Killer (NK) Activity and Antibody Dependent Cellular Cytotoxicity (ADCC) by Lipomodulin, A Phospholipase Inhibitory Protein, The Journal of Immunology, vol. 131, No. 2, Aug. 1983, pp. 662–665.

Perussia et al., Human Natural Killer Cells Analyzed by B73.1, A Monoclonal Antibody Blocking Fc Receptor Functions, The Journal of Immunology, vol. 130, No. 5, May 1983, pp. 2133–2141.

Seaman, Human Natural Killer Cell Activity is Reversibly Inhibited by Antogonists of Lipoxygenation, The Journal of Immunology, vol. 131, No. 6, Dec. 1983, pp. 2953–2957.

Domzig et al., Interleukin 2 Dependence of Human Natural Killer (NK) Cell Activity, The Journal of Immunology, vol. 130, No. 4, Apr. 1983, pp. 1970–1973.

Komiyama et al., Childhood Acute Lymphoblastic Leukemia with Natural Killer Activity, Cancer 54, 1984, p. 1547.

Kleinerman et al., Tumoricidal Activity of Human Monocytes: Evidence for Cytolytic Function Distinct from that of NK Cells, The Journal of Immunology, vol. 133, No. 1, Jul. 1984, pp. 4–6.

Vadas et al., Mononuclear Cell-Mediated Enhancement of Granulocyte Function In Man, The Journal of Immunology, vol. 133, No. 1, Jul. 1984, pp. 202–207.

Calvo et al., Preferential Elimination of NK and CTL Functions by Anti-D44 Monoclonal Antibody, The Journal of Immunology, vol. 132, No. 5, May 1984, pp. 2345–2349.

Trinchieri et al., Biology of Disease, Human Natural Killer Cells: Biologic and Pathologic Aspects, Laboratory Investigation, vol. 50, No. 5, 1984, pp. 489–513.

London et al., Induction of Proliferation In Vitro of Resting Human Natural Killer Cells: Expression of Surface Activation Antigens, The Journal of Immunology, vol. 134, No. 2, Feb. 1985, pp. 718–727.

Holmbert et al., Aug. 1984, The Effect of Natural Killer Cells on the Development of Syngeneic, Hematopoietic Progenitors, pp. 2933–2939.

USE OF DIPEPTIDE ALKYL ESTERS TO TREAT GVHD

This is a continuation of U.S. Ser. No. 774,051, filed Sept. 9, 1985 and issued as U.S. Pat. No. 4,752,602, June 21, 1988.

BACKGROUND OF THE INVENTION

The present invention concerns certain dipeptide esters and their users, particularly for ablation of certain cell-mediated immune responses. For brevity and clarity, many of the terms used herein have been abbreviated and these abbreviations include those shown in Table 1. Research involved in the development of the invention was supported by grants from the United States government.

L-leucine methyl ester (Leu-OMe) has previously been used as a lysosomotropic agent (Thiele et al. (1983) J. Immunol. V 131, pp 2282-2290; Goldman et al. (1973) J. Biol. Chem. V 254, p 8914). The generally accepted lysosomotropic mechanism involved leu-OMe diffusion into cells and into lysosomes, followed by intralysosomal hydrolysis to leucine and methanol. The more highly ionically charged leucine, largely unable to diffuse out of the lysosome, caused osmotic lysosomal swelling and rupture. The fate of leu-OMe subjected to rat liver lysosomes was additionally suggested by Goldman et al. (1973) to involve a transpeptidation reaction and a resultant species—"presumably the dipeptide" which was "further hydrolyzed to free amino acids". A subsequent and related paper by Goldman (FEBS (Fed. Europ. Biol. Sci.) Letters V 33, pp 208-212 (1973)) affirmed that non-methylated dipeptides were thought to be formed by lysosomes.

L-amino acid methyl esters have been specifically shown to cause rat liver lysosomal amino acid increases (Reeves (1979) J. Biol. Chem. V 254, pp 8914-8921). Leucine methyl ester has been shown to cause rat heart lysosomal swelling and loss of integrity (Reeves et al., (1981) Proc. Nat'l. Acad. Sci., V 78, pp 4426-4429).

TABLE 1

| Abbreviations | Symbol |
|---|---|
| Substance | |
| L-leucine | leu |
| L-phenylalanine | phe |
| L-alanine | ala |
| L-glycine | gly |
| L-serine | ser |
| L-tyrosine | tyr |
| L-arginine | arg |
| L-lysine | lys |
| L-valine | val |
| L-isoleucine | ile |
| L-proline | pro |
| L-glutamic acid | glu |
| L-aspartic acid | asp |
| L amino acid methyl esters | e.g. Leu—OMe |
| L amino acid ethyl esters | e.g. Leu—OEt |
| D-amino acids | e.g. D-Leu |
| D-amino acids methyl esters | e.g. D-Leu—OMe |
| dipeptides of L-amino acids | e.g. Leu—Leu |
| methyl esters of dipeptide L amino acids | e.g. Leu—Leu—OMe |
| cell fraction or type | |
| mononuclear phagocytes | MP |
| polymorphonuclear leucocytes | PMN |
| natural killer cells | NK |
| peripheral blood mononuclear cells | PBM |
| cytotoxic T-lymphocytes | CTL |
| glass or nylon wool adherent cells | AC |

TABLE 1-continued

| Abbreviations | Symbol |
|---|---|
| glass or nylon wool non-adherent cells | NAC |
| Other Materials | |
| phosphate buffered saline | PBS |
| thin layer chromatography | TLC |
| fluorescence activated cell sorter | FACS |
| mixed lymphocyte culture | MLC |
| Miscellaneous | |
| effector:target cell ratio | E:T |
| fetal bovine serum | FBS |
| University of Texas Health Science Center, Dallas, Texas. | UTHSCD |
| Standard error of mean | SEM |
| probability of significant difference (Student's t-test) | p |
| Graft versus host disease | GVHD |

Natural killer cells are large granular lymphocytes that spontaneously lyse tumor cells and virally-infected cells in the absence of any known sensitization. This cytotoxic activity can be modulated by a host of pharmacologic agents that appear to act directly on NK effector cells. NK activity has been shown to be augmented after exposure to interferons (Gidlund et al., Nature V 223, p 259), interleukin 2, (Dempsey, et al. (1982) J. Immunol. V 129, p 1314) (Domzig, et al. (1983) J. Immunol. V 130, p 1970), and interleukin 1 (Dempsey et al.. (1982) J. Immunol. V 129, p 1314), whereas target cell binding is inhibited by cytochalasin B. (Quan, et al. (1982) J. Immunol. V 128, p 1786), dimethyl sulfoxide, 2-mercaptoethanol, and magnesium deficiency (Hiserodt, et al. (1982) J. Immunol. V 129, p 2266). Subsequent steps in the lytic process are inhibited by calcium deficiency (Quan et al. (1982) J. Immunol. V 128, p 1786, Hiserodt, et al. (1982) J. Immunol. V 129, p 2266), lysosomotropic agents (Verhoef, et al. (1983) J. Immunol. V 131, p 125), prostaglandin $E_2$ ($PGE_2$) (Roder, et al. (1979) J. Immunol. V 123, p 2785, Kendall, et al. (1980) J. Immunol. V 125, p 2770), cyclic AMP (Roder, et al. (1979) J. Immunol. V 123, p 2785, Katz (1982) J. Immunol. V 129, p 287), lipomodulin (Hattori, et al. (1983) J. Immunol. V 131, p 662), and by antagonists of lipoxygenase (Seaman (1983) J. Immunol V 131 p 2953). Furthermore, it has been demonstrated that $PGE_2$ and reactive metabolites of oxygen produced by monocytes (MP) or polymorphonuclear leukocytes (PMN) can inhibit NK cell function (Koren, et al. (1982) Mol. Immunol. V 19, p 1341; and Seaman, et al. (1982) J. Clin. Invest. V 69, p 876).

Previous work by the present applicants has examined the effect of L-leucine methyl ester on the structure and function of human peripheral blood mononuclear cells (PBM) (Thiele, et al. (1983) J. Immunol. V 131, p 2282.

Human peripheral blood mononuclear cells (PBM) are capable of mediating a variety of cell-mediated cytotoxic functions. In the absence of any known sensitization, spontaneous lysis of tumor cells and virally-infected cells is mediated by natural killer cells (NK) contained within the large granular lymphocyte fraction of human PBM Timonen et al.. (1981) v. J. Exp Med. V 153 pp 569-582. After lymphokine activation, additional cytotoxic lymphocytes capable of lysing a broad spectrum of tumor cell targets can be generated in in vitro cultures (Seeley et al. (1979) J. Immunol. V 123, p 1303; and Grimm et al. (1982) J. Exp. Med. V 155, p 1823). Furthermore, lymphokine activated peripheral blood mononuclear phagocytes (MP) are also capable of lysing certain tumor targets (Kleinerman et al. (1984) J. Immunol. V 133, p 4). Following antigen-specific stimulation, cell-mediated lympholysis can be mediated by cytotoxic T lymphocytes (CTL).

While a variety of functional and phenotypic characteristics can be used to distinguish these various types of cytotoxic effector cells, a number of surface antigens and functional characteristics are shared. Thus, the antigens identified by the monoclonal antibodies OKT8 (Ortaldo et al. (1981) J. Immunol. V 127, p 2401; and Perussia et al. (1983) J. Immunol. V 130, p 2133), OKT11 (Perussia et al. (1983) J. Immunol. V 130, p 2133; and Zarling et al. (1981) J. Immunol. V 127, p 2575), NK9 (Nieminen et al. (1984) J. Immunol. V 133, p 202) and anti-D44 (Calvo et al. (1984) J. Immunol. V 132, p 2345) are found on both CTL and NK while the antigen identified by OKM1 is shared by MP and NK (Zarling et al. (1981) J. Immunol. V 127, p 2575; Ortaldo et al. (1981) J. Immunol. V 127, p 2401; Perussia et al. (1983) J. Immunol. V 130, p 2133; and Breard et al. (1980) J. Immunol. V 124, p 1943. Furthermore, cytolytic activity of both NK and MP is augmented by interferons, (Kleinerman et al. (1984) J. Immunol. V 133, p 4; Gidlund et al. (1978) Nature V 223, p 259; and Trinchieri et al. (1978) J. Exp. Med. V 147, p 1314). Finally, use of metabolic inhibitors has demonstrated some parallels in the lytic mechanism employed by CTL and NK (Quan et al. (1982) J. Immunol. V 128, p 1786; Hiserodt et al. (1982) J. Immunol. V 129, p 1782; Bonavida et al. (1983) Immunol. Rev. V 72, p 119; Podack et al. (1983) Nature V 302, p 442; Dennert et al. (1983) J. Exp. Med. V 157, p 1483; and Burns et al. (1983) Proc. Nat'l. Acad. Sci. V 80, p 7606).

SUMMARY OF THE INVENTION

An alkyl ester of dipeptides consisting essentially of natural or synthetic L-amino acids with hydrophobic side chains. Preferable amino acids are leucine, phenylalanine, valine, isoleucine, alanine, proline, glycine or aspartic acid beta methyl ester. Preferable dipeptides are L leucyl L-leucine, L-leucyl L-phenylalanine, L-valyl L-phenylalanine, L-leucyl L-isoleucine, L-phenylalanyl L-phenylalanine, L-valyl L-leucine, L-leucyl L-alanine, L-valyl L-valine, L-phenylalanyl L-leucine, L-prolyl L-leucine, L-leucyl L-valine, L-phenylalanyl L-valine, L glycyl L-leucine, L-leucyl L-glycine or L-aspartyl beta methyl ester L-phenylalanine. The most preferable dipeptides are L-leucyl L-leucine, L-leucyl L-phenylalanine, L-valyl L-phenylalanine, L-phenylalanyl L-leucine, L-leucyl L-isoleucine, L-phenylalanyl L-phenylalanine and L-valyl L-leucine.

The alkyl ester of the dipeptide is most preferably a methyl ester and may also be an ethyl ester or alkyl of up to about four carbon atoms such as propyl, isopropyl, butyl or isobutyl.

DETAILED DESCRIPTION OF PREFERRED EMBODIMENTS

Figure 1:
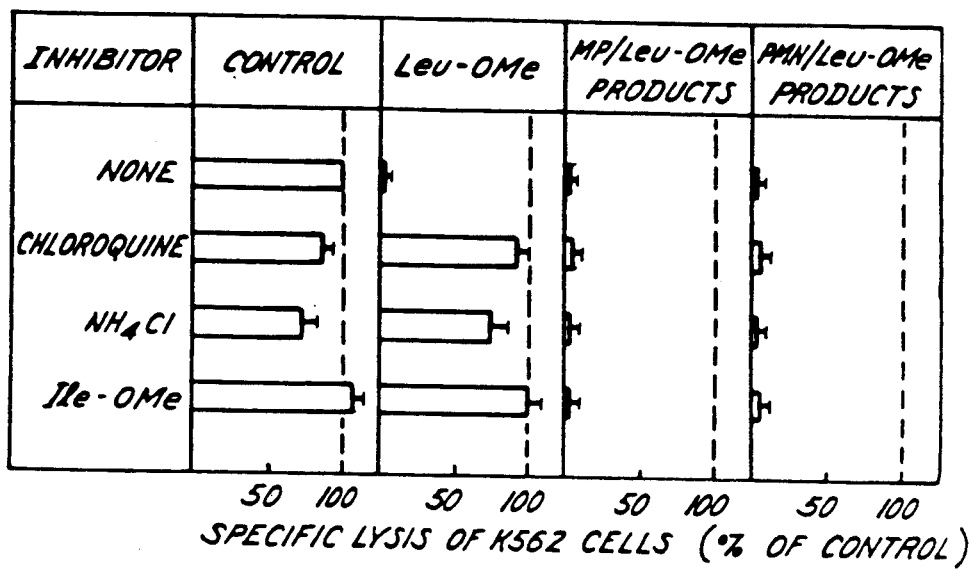
FIG. 1 shows that whereas ablation of NK function during incubation with Leu-OMe can be blocked by lysosomotropic agents, there is a product formed during incubation of Leu-OMe with MP or PMN which has effects on NK function no longer blocked by lysosomal inhibitors.

The present invention concerns new compounds and their uses in ablating particular cell types and their functions. The presently described invention relates to the discovery that dipeptide alkyl esters are cytotoxic metabolites of lysosomotropic amino acid alkyl esters.

It has further been found that alkyl esters of dipeptides consisting essentially of natural or synthetic amino acids with hydrophobic side chains may function cytotoxically to deactivate natural killer cells (NK) and cytotoxic T lymphocytes (CTL). By the term "hydrophobic" as used herein, is meant uncharged in aqueous solution at physiological pH and also as having no hydroxyl, carboxyl or primary amino groups.

Treatment of NK or CTL with an effective level of an alkyl ester of a dipeptide consisting essentially of natural or synthetic amino acids with hydrophobic side chains serves to deactivate the cytotoxic functions of said cells. An effective level varies from circumstance to circumstance but generally lies between about 25 micromolar and about 250 micromolar. An effective level for a whole animal dose generally lies between about 100 mg/kg and about 300 mg/kg.

Both methyl and ethyl esters of dipeptides consisting essentially of natural or synthetic amino acids having hydrophobic side chains have been specifically found to deactivate natural killer cells or cytotoxic T lymphocytes and other alkyl esters of these dipeptides are confidently predicted to have similar or superior effects.

Deactivation of natural killer cells (NK) or CTL cells with such dipeptide alkyl esters should increase the success of allogeneic bone marrow transplants by lowering the incidence of graft-versus-host disease (GVHD) and by lowering the incidence of transplant rejection.

Graft versus host disease (GVHD) is a major problem in allogeneic bone marrow transplantation. It occurs in approximately 70% of transplant recipients and causes death in 20% of those (Wells, et al. p 493 in Basic and Clinical Immunology. Fundenbergo et al. (editors) 2nd ed. Lange, (1978)). The disease occurs when cells of the graft (donor) attack the host tissue, causing abnormalities in the immune system and gastrointestinal tract, as well as skin rashes and liver dysfunction. Although cytotoxic T lymphocytes have traditionally been considered to be the primary effector cells in GVHD, recent studies have shown a correlation between the occurrence of the disease and the appearance of NK activity soon after transplantation. These results implicate the donor's NK cells in the etiology of GVHD. Moreover, other studies demonstrate that high levels of NK activity in a bone marrow recipient prior to transplantation are associated with GVHD (Dokhelar et al. (1981) Transplantation V 31 p 61; Lopez et al. (1979) Lancet V 2 p 1103; and Lopez et al. (1980) Lancet V 2 p 1025). Thus, it is theorized that both host and donor NK cells contribute to the development of the disease.

Current regimens for the prevention and treatment of GVHD consist of depleting T-lymphocytes from the donor marrow prior to transplantation and giving the recipient immunosuppressive drugs such as cyclophosphamide and methotrexate, both before and after transplantation. The effectiveness of these regimens might be enhanced by treating donor bone marrow and transplant recipients with dipeptide methyl esters. Potential problems with these procedures include possible non-specific toxicity of therapeutic dipeptide alkyl esters and the re-emergence of NK activity from precursors not sensitive to therapeutic dipeptide alkyl esters.

Currently, bone marrow transplantation is used as a major mode of therapy in treating aplastic anemia, acute myelogenous leukemia, and a variety of immunodeficiency states. As mentioned above, a major complication of this therapy is graft-versus-host disease (Sullivan et al., Blood V 57, p 207). Severity of GVHD in man correlates with pretransplant levels of natural killer (NK) activity (Lopez et al., Lancet V 2, p 2101). Thus, by virtue of its ability to diminish NK function in vivo, it is contemplated that Leu-Leu-OMe administration, for example, to bone marrow samples prior to their transplantation will be efficacious in diminishing this complication. An effective level of the dipeptide alkyl esters of the present invention for in vitro deactivation of natural killer cells is between about 10 micromolar and about 250 micromolar.

Furthermore, in both murine and human models, the incidence of GVHD is decreased by in vitro treatment of donor bone marrow with agents that deplete mature T cells (Korngold et al., Exp. Med. V 148, p 1687; Reisner et al., Blood V 61, p 341). Since cytotoxic T cells (CTL) derived from donor bone marrow appear to be the final mediators of GVHD, in vitro treatment of donor bone marrow with an agent which selectively damages cytotoxic T cell precursors is also likely to be of benefit. Since such an in vitro action of Leu-Leu-OMe has now been demonstrated it is expected that this agent will be of benefit in pretreating donor bone marrow. An effective level of the dipeptide alkyl esters of the present invention for treatment of bone marrow to be transplanted should be between about 10 micromolar and 250 micromolar for ablation of GVHD-mediating CTL and NK.

A second problem in bone marrow transplantation is the failure of engraftment (the transplant does not "take" or is rejected). This problem occurs in 10-20% of transplants and can be caused by several factors, including improper transplantation technique, extensive invasion of the recipient's bone marrow by tumor cells, and rejection of the transplant.

The discovery that $F^1$ mice could reject transplants of parental bone marrow first indicated that NK cells might be involved in the engraftment failures (Cudkowicz et al. (1971) J. Exp. Med. V 134, p 83; Cudkowicz et al. (1971) J. Exp. Med. V 134, p 1513; and Kiessling et al. (1977) Eur. J. Immunol. V 7, p 655).

Initially graft rejection was thought to be almost totally dependent on T lymphocytes. However, T cells from an $F^1$ hybrid animal do not normally attack parental tissue. Therefore, it was suggested that NK cells, not T cells, mediated the rejection of the parental bone marrow.

Additional support for this hypothesis was derived from the observation that mice of a strain normally incapable of rejecting bone marrow transplants acquire this ability when they are injected with cloned NK cells. (Warren et al. (1977) Nature V 300, p 655,). As a result of these findings, Herberman et al. ((1981) Science V 214), p 24 have suggested that suppression of NK activity might lower the incidence of transplant rejection. This suppression should be achieved by treating the recipient with the dipeptide methyl esters of the present invention prior to transplantation.

Other clinical uses for alkyl esters of dipeptides consisting essentially of amino acids with hydrophobic side chains, or other situations where NK or CTL are involved in the pathogenesis of disease. In organ transplants in general (kidney, heart, liver, pancreas, skin, etc.) it is widely accepted that cytotoxic T cells are likely to be the cell type responsible for graft rejection (Mayer et al., J. Immunol. V 134, p 258). Thus, it is contemplated that the in vivo administration of Leu-Leu-OMe or similar dipeptide esters of the present invention will be of benefit in preventing allograft rejection.

It is also contemplated that Leu-Leu-OMe or other alkyl dipeptide esters may be of benefit in other spontaneously occurring disease states. A variety of diseases have been classified as "autoimmune diseases" because of the widely accepted belief that they are caused by disorders in the immune system which cause immunologic damage to "self". Thus, in a variety of diseases, including primary biliary cirrhosis, systemic lupus erythematosus, rheumatoid arthritis, multiple sclerosis, autoimmune hemolytic anemia, etc., various forms of immunologic damage to selected organs occur. In some of these diseases, such as primary biliary cirrhosis, the histologic abnormalities which occur (in this case in the liver) closely resemble those which occur in GVHD or in rejection of a transplanted liver (Fennel, (1981), Pathol. Annu. V 16 p 289. Thus, it is reasonable that similar mechanisms of cytotoxic lymphocyte damage to liver cells may be occurring, and therefore benefit from therapy with Leu-Leu-OMe or other dipeptide alkyl esters of the present invention should also occur in such disease states.

The dipeptide alkyl esters of the present invention should be usable chemotherapeutic agents in patients with natural killer cell tumors (generally leukemias), although very few reports of these tumors are found in the literature (Komiyama et al., (1982) Blood V 60, p 1428 (1982); Itoh et al. (1983) Blood V 61, p 940; Komiyama et al. (1984) Cancer V 54 p 1547.

It is contemplated that the dipeptide alkyl esters of the present invention may also be used to treat patients with aplastic anemia and other types of bone marrow dysfunction. This suggestion is based on three sets of observations in human studies: first, NK cells can kill normal bone marrow cells (Hansson, et al. (1981) Eur. J. Immunol. V 11, p 8); second NK cells inhibit growth of blood cell precursors in vitro (Hansson, et al. (1982) J. Immunol. V 129, p 126; Spitzer et al.: Blood V 63, p 260; Torok-Storb et al. (1982) Nature V 298, p 473; Mangan, et al. Blood V 63, p 260); and third, NK-like cells with the ability to inhibit the formation of red blood cells with the ability to inhibit the formation of red blood cells have been isolated from patients with aplastic anemia (Mangan, et al. (1982) J. Clin. Invest. V 70, p 1148; and Nogasawa et al. (1981) Blood V 57, p 1025). Moreover, recent studies in the mouse indicate that NK cells may function to suppress hemopoiesis in vivo (Holmberg et al. (1984) J. Immunol. V 133, p 2933). However, further investigation is desireable before the connection between NK activity and bone marrow dysfunction is considered conclusive.

Generally, when the dipeptide alkyl esters of the present invention are administered to animals, an effective level is between about $1 \times 10^{-4}$ moles/kg and about $1 \times 10^{-2}$ moles/kg.

The following Examples are presented to more fully illustrate preferred embodiments of the present invention and are not intended to limit the invention uless otherwise so stated in the accompanying claims.

EXAMPLE 1

Cell Preparations and Assays

PBM were separated from heparinized venous blood of healthy donors by centrifugation over sodium diatrizoate-Ficoll gradients (Isolymph, Gallard-Schlesinger Chemical Mfg. Corp., Carle Place, N.Y.). Monocyte-enriched populations ((MP) were prepared from glass adherent cells and MP-depleted lyphocytes from the nonadherent cells remaining after incubation in glass Petri dishes and passage through nylon wool columns as detailed in Rosenberg et al. (1975) (J. Immunol V 122, pp 926-831). PMN were collected by resuspending peripheral blood cells that penetrated sodium diatrizoate-Ficoll gradients and removing erythrocytes nu dextran sedimentation and hypotonic lysis as previously outlined (Thiele et al. (1985) J. Immunol. V 134, pp 786-793.

All cell exposures to the amino acids, dipeptides or their methyl esters were carried out by suspending cells in Dulbecco's phosphate buffered saline (PBS) and incubating them at room temperature with the reagent at the indicated concentration and time interval. After incubation, the cells were washed twice with Hanks' balanced salt solution and resuspended in medium RPMI 1640 (Inland Laboratories, Fort Worth, Tex.) supplemented with 10% fetal bovine serum (Microbiological Associates, Walkersville, Minn.) for assay of function.

Natural killing against K562 target cells was assessed by a 3 hour $^{51}$Cr release assay and percent specific lysis calculated as previously described (Thiele et al. (1985) J. Immunol. V 134, pp 786-793). Percent of control cytotoxicity was calculated using the formula:

$$\frac{\text{Experimental \% specific lysis}}{\text{Control \% specific lysis}} \times 100$$

EXAMPLE 2

General Procedures for Generation, Purification and Characterization of L-leucine Methyl Ester and Its Metabolites MP or PMN (prepared as in Example 1) at a concentration of $25 \times 10^6$ per ml were suspended in PBS and incubated with 25 mM Leu-OMe for 20 minutes at 22° C. Cell suspensions were then centrifuged at 1000 g for 10 minutes and the supernatants harvested and freeze-dried at −70° C., 100 millitorr atmospheric pressure. In some experiments, Leu-OMe-treated MP or PMN were sonicated to increase the yield of the reaction product. Samples were then extracted with methanol for application to thin layer chromatography (TLC) plates (200 micromolar × 20 cm$^2$, Analtech, Newark, Del.). Following development with chloroform/methanol/acetic acid (19:1:12.5 by volume), 1 cm bands were eluted with methanol, dried under nitrogen, and resuspended in 1 ml PBS. Mass spectra were obtained with a Finnegan Model 4021 automated EI/CI, GC/MS system coupled to an Incos data system. Methane was used as the reagent gas for chemical ionization (CI)mass spectral analysis.

EXAMPLE 3

Lysosomotropic Substances and Formation of NK-toxic Products

The addition of Leu-OMe to human PBM was shown to cause rapid death of MP and NK cells but not T or B lymphocytes (Thiele et al. (1985) J. Immunol. V 134, pp 786-793; Thiele et al. (1983) J. Immunol. V 131, pp 2282-2290). Amino acid methyl esters are known to be lysosomotropic compounds, and in previous studies it was found that the lysosomal inhibitors, chloroquine and NH$_4$Cl, prevented Leu-OMe-induced MP toxicity. To assess whether these agents similarly prevented formation of any NK toxic products, the following experiments were carried out, and the results shown in FIG. 1.

PBM (prepared as in Example 1) were incubated with various potential NK toxic agents in the presence or absence of various lysosomal inhibitors for 40 minutes, washed to remove the inhibitor, incubated for 18 hours to permit recovery from any transient inhibition caused by lysosomotropic agents and then tested for NK activity. As can be seen in FIG. 1, neither chloroquine, NH$_4$Cl, nor Ile-OMe had any substantial permanent effect on NK function. In contrast, 5 mM Leu-OMe ablated all NK activity. This activity of Leu-OMe was largely prevented by chloroquine, NH$_4$Cl, or Ile-OMe. The products generated by MP or PMN, after exposure to Leu-OMe also completely removed all NK activity from PBM. In contrast to the effect noted with Leu-OMe, the lysosomal inhibitors did not protect NK cells from the action of this product(s). Additional experiments indicated that the sonicates of MP or PMN had no effect on NK function in this system whereas the supernatants or sonicates of Leu-OMe treated PMN or MP also depleted NK cells from MP depleted lymphocytes. These results therefore suggest that interaction of Leu-OMe with the lysosomal compartment of MP or PMN produced a product which was directly toxic to NK cells through a mechanism that was no longer dependent on lysosomal processing within the NK cell or an additional cell type.

More particularly, the conditions of the manipulations leading to the results shown in FIG. 1 were as follows:

Inhibitors of lysosomal enzyme function prevent generation of an NK toxic product. PBM ($5 \times 10^6$/ml) or PMN ($25 \times 10^6$/ml) preincubated with 25 mM Leu-OMe for 30 minutes were added to cells to be ablated. Cells were incubated with these agents for another 30 minutes at 22° C., then washed and cultured for 18 hours at 37° C. before assay of the ability to lyse K562 cells. Data are expressed as percentage of control cytotoxicity observed with an effector:target ratio of 40:1 (results at other E:T were similar).

EXAMPLE 4

Ablation of NK Function by PMN Produced Leu OMe Product

Figure 2:
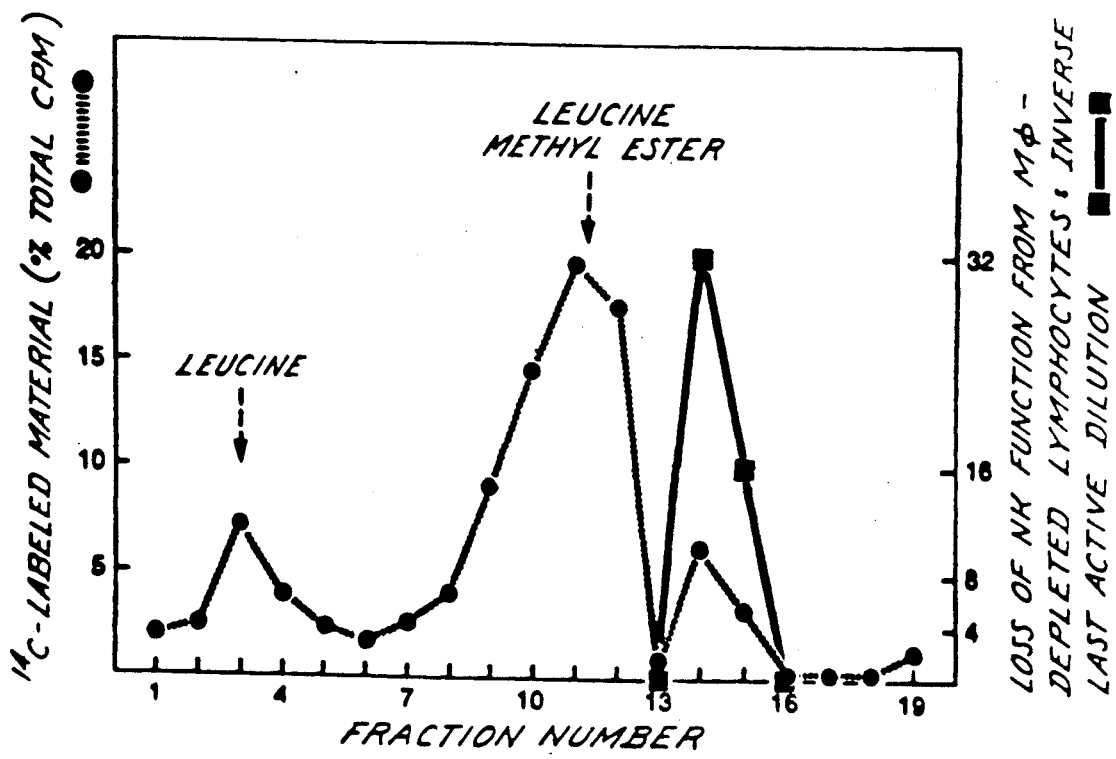
FIG. 2 shows Leu-OMe products of PMN in terms of radioactivity and NK suppressive effects of TLC fractions.

When the NK toxic properties of MP-Leu-OMe, or PMN-Leu-OMe incubation mixtures were evaluated, it was found that this activity was stable in aqueous solutions for more than 48 hours at 4° C., but labile at 100° C., retarded on Sephadex G-10 columns; dialyzable through 1000 MWCO (molecular weight cut-off) membranes, and could be extracted by chloroform-methanol (3:1, by volume). As shown in FIG. 2, when $^{14}$C-leucine methyl ester was incubated with PMN and the supernatants subsequently separated by TLC, three major peaks of $^{14}$C activity were found. One of these peaks corresponded to leucine methyl ester itself and one to free leucine while the third represented a new product. This third peak accounted for about 10% of the total $^{14}$C-labeled material. When MP-depleted lymphocytes were exposed to each TLC fraction, the third peak was found to contain all NK toxic activity. This NK toxic activity not only appeared to be $^{14}$C labeled but was also ninhydrin positive, suggesting that it was a metabolite which still retained an amino group as well as part of the carbon structure of Leu-OMe. An identical $^{14}$C labeled ninhydrin positive product was detected by TLC of MP-Leu-OMe incubation mixture supernatants or sonicates. The production by PMN or MP of this metabolite was inhibited by chloroquine, NH$_4$Cl, or Ile-OMe (data not shown).

Ablation of NK function is mediated by a metabolite of Leu-OMe. PMN ($25 \times 10^6$/ml) were incubated with 25 mM $^{14}$C-Leu-OMe for 30 minutes and supernatants harvested for 1 TLC analysis. MP-depleted lymphocytes ($2.5 \times 10^6$ cells/ml) were exposed to varying dilutions of each TLC fraction for 30 minutes, washed and cultured for 2 hours prior to cytotoxicity assay at E:T ratio of 20:1. Samples were considered to contain an NK toxic product when percent specific lysis was less than 25% of control. FIG. 2 shows these results.

EXAMPLE 5

Characterization of the NK-toxic Metabolite

Figure 3:
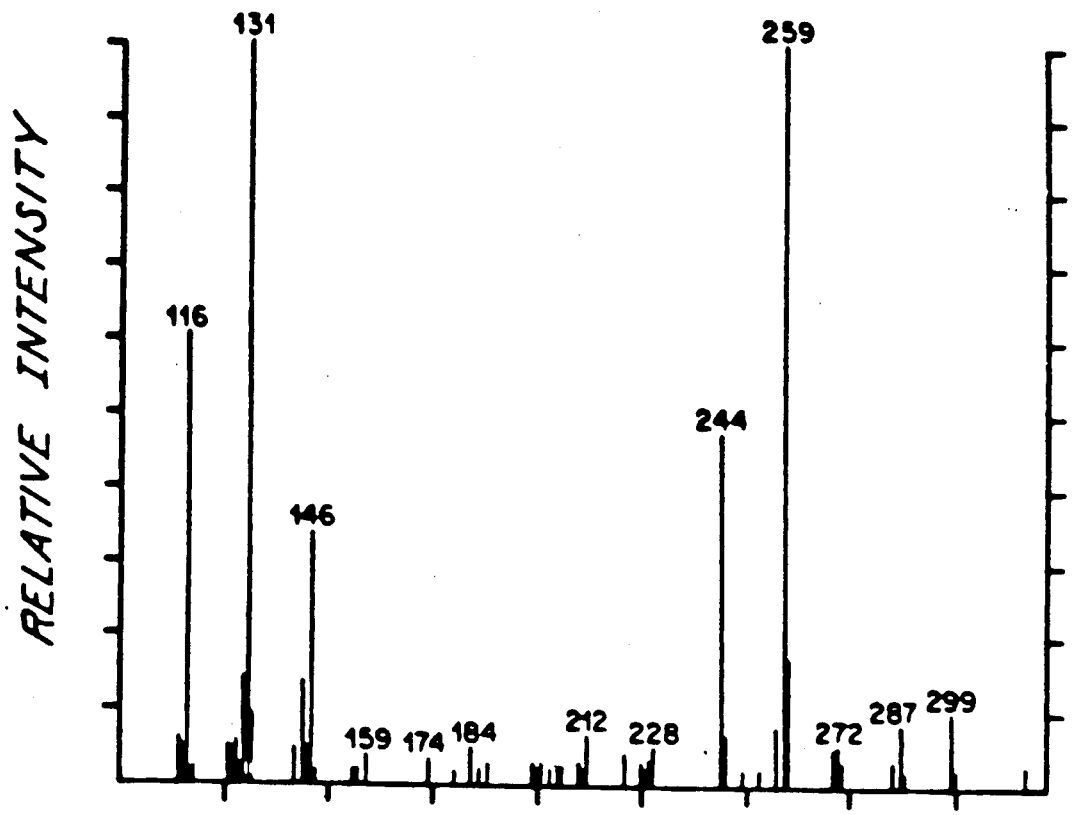
FIG. 3A shows the CI mass spectrum of a TLC-purified NK-toxic fraction.
FIG. 3B shows the CI mass spectrum of synthetic Leu-Leu-OMe.
Figure 3:
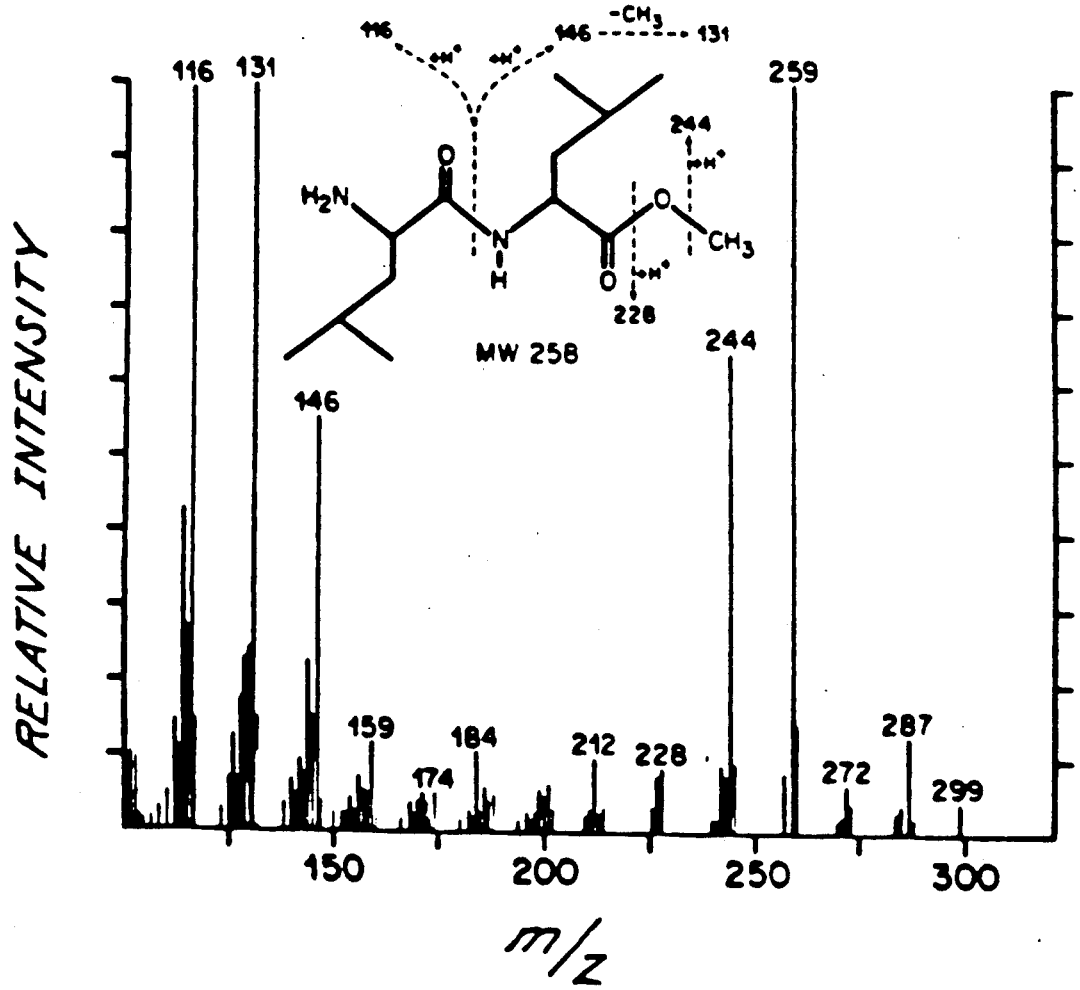

The nature of the new TLC peak found as described in Example 4 was examined by mass spectroscopy. As shown in FIG. 3A, when the TLC-purified, NK-toxic fraction was subjected to more spectral analysis, results showing peaks at M/Z 259 (MN+), 287 (M+C$_2$H$_5$+) and 299 (M+C$_3$H$_5$+)) indicated the presence of a compound of molecular weight 258. The presence of peaks at M/Z 244 (M+ −CH$_3$) and 272 (M+C$_2$H$_5$5+ −CH$_3$) suggested that this compound contained a methyl ester group. Furthermore, the persistence of peaks corresponding to leucine (MN+ =131, M+C$_2$H$_5$=159) and leucine methyl ester (MH+ =146, M+C$_2$H$_5$30=174) in spite of careful TLC purification of the NK toxic product from any free leucine or Leu-OMe present in the crude supernatants of the incubation mixtures suggested that a condensation product of Leu-OMe such as Leu-Leu-OMe (MW258) was present in the NK toxic fraction isolated after incubation of PMN or MP with Leu-OMe.

When Leu-Leu-OMe was synthesized from reagent grade Leu-Leu, by incubation in methanol hydrochloride, it was found to have TLC mobility identical to NK toxic fractions of MP-Leu-OMe or PMN-Leu-OMe incubation mixtures. Furthermore, its CI mass spectrum as shown in FIG. 3B was identical to that of the 258 molecular weight compound found in these incubation fractions.

Experiments further confirmed that Leu-Leu-OMe was the product generated by MP or PMN from Leu-OMe that was responsible for the selective ablation of NK function from human lymphocytes. Leu-Leu-OMe was synthesized by addition of Leu-Leu to methanolic HCl. TLC analysis revealed less than 2% contamination of this preparation with leucine, Leu-Leu, or leu-OMe, and CI mass spectral analysis (FIG. 3B) revealed no contaminants of other molecular weights.

FIG. 3A shows the chemical-ionization CI mass spectra of TLC fractions with NK toxic activity as described in FIG. 2, and also of Leu-Leu-OMe synthesized from reagent grade Leu-Leu (FIG. 3B).

EXAMPLE 6

Figure 4:
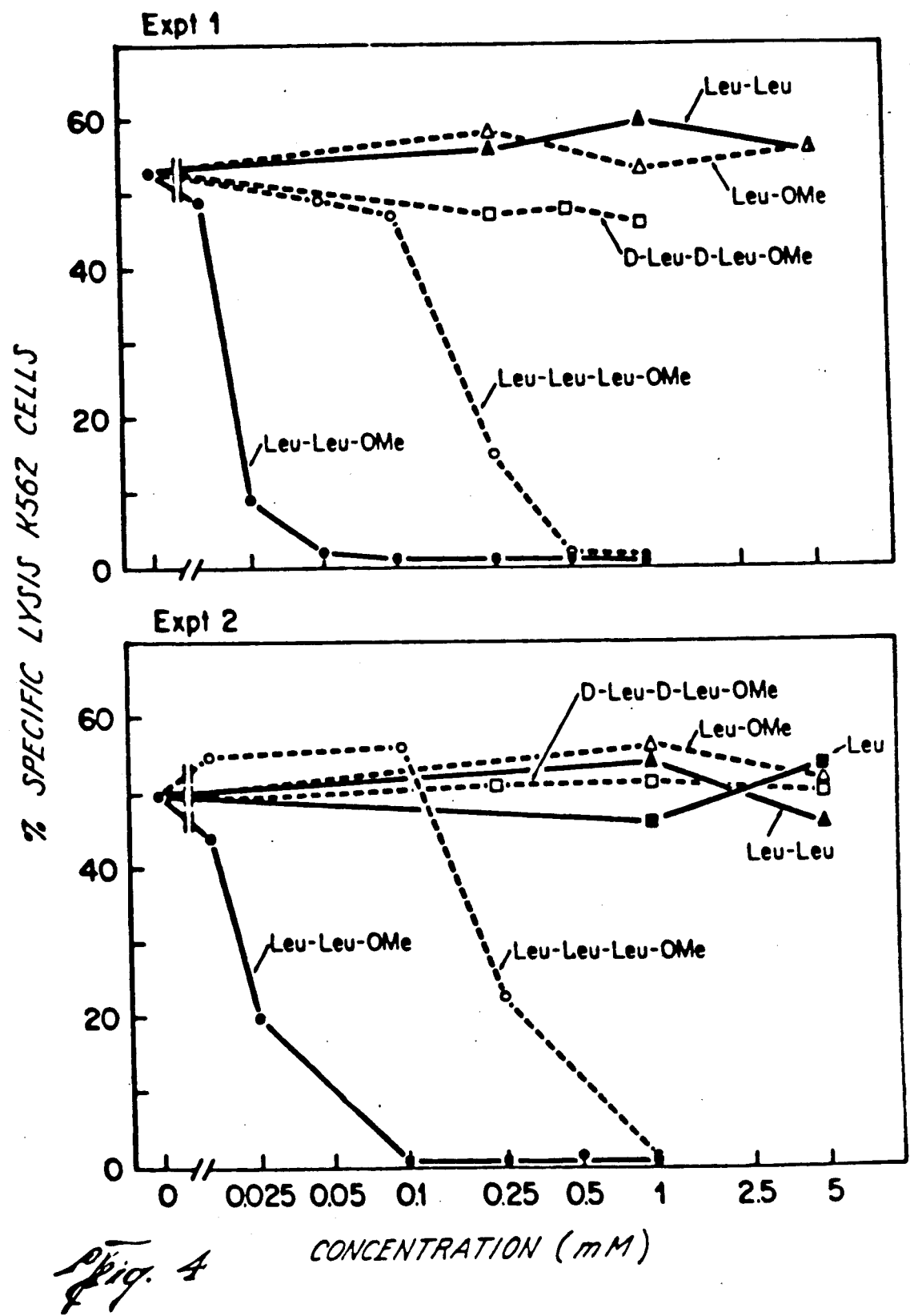
FIG. 4 shows the effects of various agents on losses of NK function from MP-depleted lymphocytes.

In the representative experiments shown in FIG. 4, MP-depleted lymphocytes were exposed to varying concentrations of Leu-Leu-OMe for 15 minutes at room temperature, then washed and assayed for ability to lyse K562 cells. No NK function could be detected in lymphocyte populations exposed to greater than 50 micromolar Leu-Leu-OMe. As previously demonstrated (Thiele et al. (1983) J. Immunol. V 131 pp 2282–2300), exposure of such MP-depleted lymphocyte populations to 100 fold greater concentration of leucine or leu-OMe had no irreversible effect on NK function. Leu-Leu or the D-stereoisomer, D-Leu-D-Leu-OMe. also had no inhibitory effect. While Leu-Leu-Leu-OMe caused dose-dependent loss of NK function, 5fold greater concentrations of this tripeptide methyl ester were required to cause an effect equivalent to that of the dipeptide methyl ester of L-leucine. When lymphocyte populations exposed to varying concentrations of Leu-Leu-OMe were further analyzed, it was found that exposure to more than 50 micromolar Leu-Leu-OMe resulted in the loss of K562 target binding as well as complete depletion of cells stained by Leu 11b, and anti-NK cell monoclonal antibody (data not shown). Thus, the MP-or PMN-generated product of Leu-OMe which is directly toxic for human NK cells is the dipeptide condensation product Leu-Leu-OMe.

The condition of the manipulations resulting in the data leading to FIG. 4 are further detailed as follows: for loss of NK function after exposure to Leu-Leu-OMe, MP-depleted lymphocytes ($2.5 \times 10^6$ cells/ml) were incubated for 15 minutes with the indicated concentrations of leucine containing compounds. Cells were then washed, cultured at 37° C. for 2 hours (Expt. 1) or 18 hours (Expt. 2) and then assayed for NK activity. Results are given for E:T ratio of 20:1.

EXAMPLE 7

NK Ablation by a Variety of Dipeptide Methyl Esters

In previously reported studies, Leu-OMe was unique among a wide variety of amino acid methyl esters in its ability to cause MP or PMN dependent ablation of NK cell function from human PBM (Thiele et al. (1985) J. Immunol. V 134, pp 786–793). The identification of Leu-Leu-OMe as the MP-generated metabolite responsible for this phenomenon suggested that either MP/PMN did not generate the corresponding dipeptide methyl esters in toxic amounts from other amino acids, or that Leu-Leu-OMe was unique among dipeptide methyl esters in its toxicity for NK cells. Therefore, experiments were carried out to assess the effect of other dipeptide methyl esters on NK cell function. The methyl esters of a variety of dipeptides were synthesized and analyzed for the capacity to deplete NK cell function. Each dipeptide methyl ester was assessed in a minimum of three esperiments. As is shown by the results displayed in FIG. 5, Leu-Leu-OMe is not the only dipeptide methyl ester which exhibits NK toxicity. When amino acids with hydrophobic side chains were substituted for leucine in either position, the resulting dipeptide methyl ester generally displayed at least some degree of NK toxicity. In particular, Leu-Phe-OMe, Phe-Leu-OMe, Val-Phe-OMe, and Val-Leu-OMe produced concentration-dependent ablation of NK function at concentrations comparable to those at which Leu-Leu-OMe was active. The sequence of active amino acids was important, however, as evidenced by the finding that Phe-Val-OMe was markedly less active than Val-Phe-OMe. Similarly, Leu-Ala-OMe was NK inhibiting, whereas 10-fold greater concentrations of Ala-Leu-OMe had no NK inhibitory effects. Furthermore, Phe-Phe-OMe was less NK toxic than either Leu-Phe-OMe or Phe-Leu-OMe and Val-Val-OMe was less active than either Leu-Val-OMe or Val-Leu-OMe, yet Val-Phe-OMe was among the most potent of the NK toxic dipeptide methyl esters. Thus, conformational aspects of the dipeptide methyl ester amino acid side chain also seem to be of importance in producing the different levels of observed NK toxicity.

Figure 5:
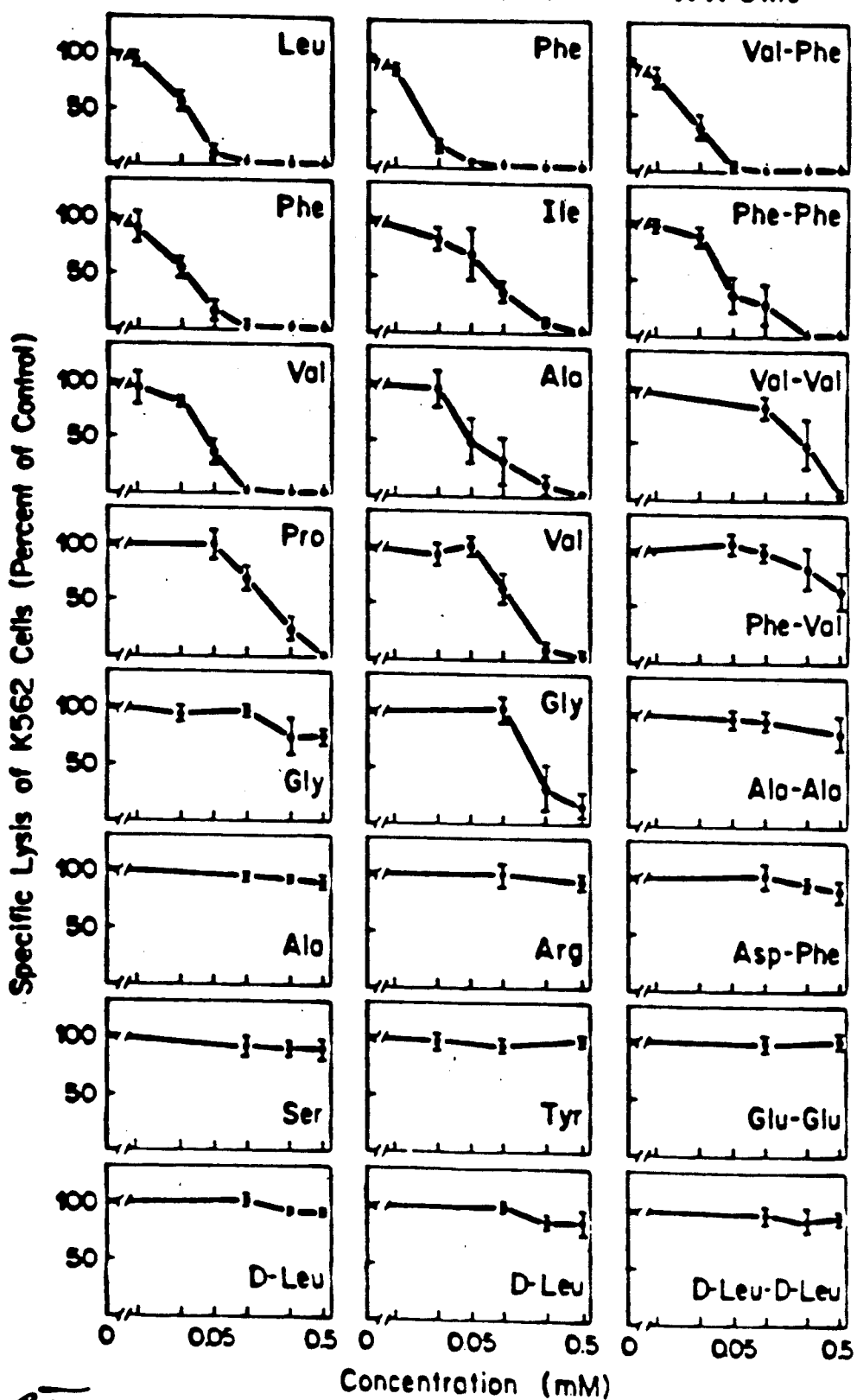
FIG. 5 shows the NK-toxicity of various dipeptide esters.

When amino acids with hydrophilic, charged or hydrogen side chains were substituted for leucine, the resulting dipeptide methyl esters either had greatly reduced NK toxicity, as in the case of Gly-Leu-OMe or Leu-Gly-OMe, or no observed NK inhibitory effects, as in the case of Leu-Arg-OMe, Leu-Tyr-OMe, Ser-Leu-OMe, Lys-Leu-OMe or Asp-Phe-OMe. Furthermore, when the D-stereoisomer was present in either position of a dipeptide methyl ester, no toxicity was observed for NK cells (FIG. 5). When unesterified dipeptides were assessed for their effect on NK function, as in the case of Leu-Leu (FIG. 4), up to $5 \times 10^{-3}$ M concentrations of Leu-Phe, Phe-Leu, Val-Leu, and Val-Phe had no effect on NK cell survival or lytic activity (data not shown).

D-Leu-D-Leu-OMe had no effect on Leu-Leu-OMe mediated NK toxicity although high levels of zinc appeared to inhibit this Leu-Leu-OMe toxicity.

Previous experiments had demonstrated that compounds such as Val-OMe, Phe-OMe, or combinations of Val-OMe and Phe-OMe did not delete NK function from human PBM (Thiele et al. (1985) J. Immunol. V 134, pp 786–793), despite the current finding that dipeptide methyl esters containing these amino acids were potent NK toxins. In order to determine whether MP or PMN could generate the relevant dipeptide methyl esters from these amino acid methyl esters, TLC analysis of the supernatants of MP and PMN incubated with these compounds was carried out. It was found that MP and PMN did generate detectable amounts of dipeptide methyl esters from these L-amino acid methyl esters. However, when equal concentrations of Leu-OMe, Val-OMe, or Phe-OMe were added to MP or PMN, the concentrations of Val-Val-OMe generated were 50 to 80% of those found for Leu-Leu-OMe, while Phe-Phe-OMe was detected at only 10–30% of the levels of Leu-Leu-OMe. Dipeptide methyl esters were not generated from D-amino acid methyl esters.

FIG. 5 shows the NK toxicity of dipeptide methyl esters. MP-depleted lymphocytes were treated with varying concentrations of dipeptide methyl esters as outlined in FIG. 4. Results are given for the mean ±SEM of at least 3 separate experiments with each compound.

EXAMPLE 8

NK Toxicity of an Artificially Hydrophobic Dipeptide Methyl Ester

Beta methyl aspartyl phenylalanine was prepared by methanolic hydrochloride methylation of aspartyl phenylalanine methyl ester. The NK toxicity of both aspartyl phenylalanine methyl ester and beta methyl aspartyl phenylalanine methyl ester was measured as described for the dipeptide methyl esters in Example 7. As the data in Table 2 indicates, when the polar side chain of the aspartyl amino acid dipeptide component is esterified with a methyl group, this being a conversion from relative hydrophilicity to substantial hydrophobicity, NK toxicity becomes apparent. Although yet not as toxically effective as a number of the hydrophobic-type dipeptides in Example 7, the data in Table 2 indicate that a dipeptide methyl ester comprising synthetic hydrophobic (lipophilic) amino acids may be used to inhibit NK function.

TABLE 2

L-ASPARTYL (beta-METHYL ESTER)-L-PHENYLALANINE METHYL ESTER IS NK TOXIC WHILE L-ASPARTYL-L-PHENYLALANINE METHYL ESTER IS NOT

| Preincubation | NK Function % Specific Cytotoxicity |
|---|---|
| Nil | 50.8 |
| Asp—Phe—OMe: | |
| 100 micromolar | 54.2 |
| 250 micromolar | 45.7 |
| 500 micromolar | 45.7 |
| 1000 micromolar | 46.9 |
| Asp-(beta-OMe)—Phe—OMe: | |
| 100 micromolar | 38.9 |
| 250 micromolar | 13.9 |
| 500 micromolar | 2.8 |
| 1000 micromolar | −0.1 |

EXAMPLE 9

In Vivo Effects on Cytotoxic Cell Function

Leu-Leu-OMe or Leu-Phe-OMe were suspended in PBS, pH 7.4. Then individual C3H/HeJ mice (25 gram size) were administered by tail-vein injection either $2.5 \times 10^{-5}$ moles (6.5 mg) of Leu-Leu-OMe, $2.5 \times 10^{-5}$ moles (7.1 mg) Leu-Phe-OMe, or an equal volume of the PBS diluent, this dose being about $1'10^{-3}$ moles per kg. For 15–30 minutes post-injection, Leu-Leu OMe and Leu-Phe OMe-treated animals but not the control animals exhibited decreased activity and an apparent increase in sleep. Subsequent to this quiescent period no difference in activity or appearance in the mice was noted. Two hours post-injection, the mice were sacrificed and their spleen cells were assayed for NK function in a standard 4 hour assay against YAC-1 tumor targets. In all mice, total cell recovery ranged from $1 \times 10^8$ to $1.1 \times 10^8$ spleen cells per animal. As noted in Table 3, the control mouse spleen cells exhibited greater killing at 25:1 and 50:1 effector to target cell ratios than did the spleen cells of treated mice at 100:1 and 200:1 E/T, respectively. Thus, Leu-Leu-OMe or Leu-Phe- OMe caused a greater than 75% decrease in splenic lytic activity against YAC-1 tumor targets.

TABLE 3

| Cytotoxic Cell Function | | | | |
| --- | --- | --- | --- | --- |
| | Effector:Target Ratio | | | |
| | 25:1 | 50:1 | 100:1 | 200:1 |
| | Percent lysis of target cells | | | |
| Control | 8.29 | 12.88 | 20.60 | 29.29 |
| Leu—Leu—OMe | 2.37 | 4.58 | 7.12 | 12.77 |
| Leu—Phe—OMe | 3.89 | 4.68 | 6.91 | 11.91 |

EXAMPLE 10

Differential Sensitivity of Natural Killer Cells (NK) and Mononuclear Phagocytes (MP) to Leucylleucine-Methyl Ester (Leu-Leu-OMe)

Figure 6:
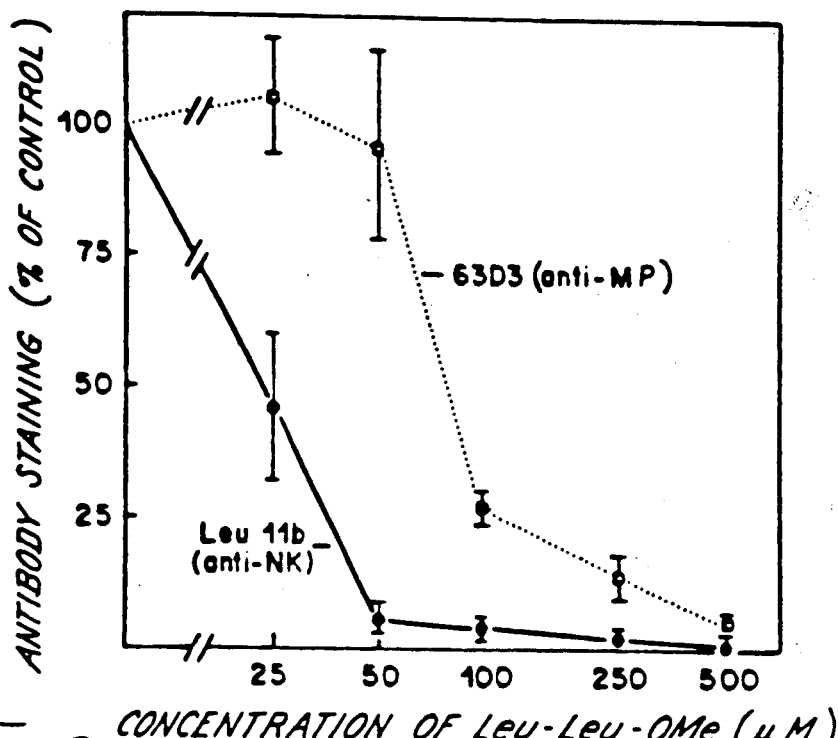
FIG. 6 shows the loss of NK and MP from PBM incubated with Leu-Leu-OMe at various concentrations.

In the experiments depicted in FIG. 6, freshly isolated PBM ($2.5 \times 10^6$/ml PBS and 1 g/l glucose) were incubated at room temperature with varying concentrations of Leu-Leu-OMe. After a 15 minute exposure to this compound, the cells were washed, incubated for 2 hours at 37° C. and then assessed for the percentage of remaining viable cells which were stained by anti-MP or anti-NK monoclonal antibodies. Preincubation with greater than 25–50 micromolar Leu-Leu-OMe led to loss of NK cells. This concentration of Leu-Leu-OMe did not deplete MP from PBM but higher concentrations of Leu-Leu-OMe caused loss of MP. The data is FIG. 6 show these results.

Anti-MP monoclonal antibodies (63D3) and anti-NK monoclonal antibodies (leu 11b) were obtained from Becton Dickinson Monoclonal Center, Inc., Mountain View, Calif. The antibody staining and Fluorescence Activated Cell Sorter (FACS) procedure was that of Rosenberg et al. (1981) (J. Immunol. V 126, p 1473). Data are expressed as percent of antibody staining in control cells (mean±SEM, n=4).

EXAMPLE 11

Effects of Leu-Leu-OMe on a Variety of Cell Types

While it was clear that a substantial percentage of lymphocytes remained viable following exposure to even 1 mM Leu-Leu-OMe, the finding that disparate cell types such as MP and NK were both susceptible to Leu-Leu-OMe mediated toxicity raised the possibility that this agent was a non-specific cell toxin. Therefore, the series of experiments depicted in FIG. 7 was performed to assess other cell types for evidence of toxicity following exposure to Leu-Leu-OMe.

To facilitate screening of multiple cell types for evidence of cell death following exposure to Leu-Leu-OMe, a $^{51}$Cr release assay was devised. In preliminary experiments it was noted that $^{51}$Cr release from MP-enriched populations exposed to varying concentrations of Leu-Leu-OMe correlated very closely with concentration-dependent loss of anti-MP antibody staining cells from PBM after similar incubation. Following brief exposures to Leu-Leu-OMe at room temperature, the loss of anti-MP antibody staining cells from PBM or the release of $^{51}$Cr from MP-enriched populations was always detectable within a 30 to 60 minute period of culture at 37° C. and maximal effects were seen within 3 to 4 hours.

Therefore, $^{51}$Cr release in a 4 hour assay was used in these experiments to assess toxicity from Leu-Leu-OMe. As shown in the first graph of FIG. 7, when the whole PBM population was exposed to varying concentrations of Leu-Leu-OMe, detectable $^{51}$Cr release was observed after exposure to 25 to 50 micromolar Leu-Leu-OMe, but only upon exposure to greater than 100 micromolar Leu-Leu-OMe was the maximal achievable $^{51}$Cr release from PBM observed. When MP-enriched adherent cells (AC) were similarly assessed, minimal $^{51}$Cr release was observed after exposure to 25–50 micromolar Leu-Leu-OMe whereas upon incubation with higher concentrations of this agent, more $^{51}$Cr release from AC was observed than with PBM. When nylon wool non-adherent lymphocytes (NAC) were assessed, small but significant $^{51}$Cr release was observed with 25 to 50 micromolar Leu-Leu-OMe. When NAC were exposed to increasing concentrations of Leu-Leu-OMe, greater quantities of $^{51}$Cr release were observed. N-SRBC positive cells showed a dose-dependent Leu-Leu-OMe induced $^{51}$Cr release pattern indistinguishable from that of NAC. Since both antibody staining (FIG. 6) and functional studies (FIG. 4) have shown that 100 micromolar Leu-Leu-OMe causes maximal depletion of NK, this finding suggested that other lymphocytes were also susceptible to Leu-Leu-OMe toxicity at concentrations greater than 100 micromolar. When T4 enriched populations of T cells were assessed, however, it was clear that even 1000 micromolar Leu-Leu-OMe caused minimal $^{51}$Cr release from this population. In contrast, when N-SRBC positive cells were depleted of OKT4 positive cells, the remaining T8-enriched population produced high levels of $^{51}$Cr release following exposure to Leu-Leu-OMe.

When cell lines of myeloid or lymphoid origin were similarly assessed, selective toxicity of Leu-Leu-OMe was again observed. The human T cell leukemia line MoLT-4 demonstrated no detectable Leu-Leu-OMe toxicity over a broad concentration range. The human plasma cell lines HS-Sultan and the B lymphoblastoid line Daudi demonstrated no significant $^{51}$Cr release or alteration in subsequent proliferaive rate (data not shown) after exposure to a broad range of Leu-Leu-OMe concentrations. When the susceptibility of EBV-transformed B cell lines or clones to this agent was assessed, no significant toxicity of less than 250 micromolar Leu-Leu-OMe was seen. However, with higher concentrations of Leu-Leu-OMe, a variable degree of toxicity was seen. Some EBV lines consistently displayed less than 20% $^{51}$Cr release even after exposure to 1 mM Leu-Leu-OMe, while other lines produced 25-35% $^{51}$Cr release after exposure to 250 micromolar Leu-Leu-OMe. In contrast, the human cell line U937 was susceptible to concentration-dependent Leu-Leu-OMe toxicity in a pattern indistinguishable from that of the peripheral blood MP with which this cell line shares many phenotypic and functional characteristics. After exposure to more than 250 micromolar Leu-Leu-OMe, extensive $^{51}$Cr release was observed and no viable proliferating U937 cell could be detected (data not shown). Similarly, the erythroleukemia line K562 demonstrated no significant $^{51}$Cr release or alteration in subsequent proliferative rate (date not shown) upon exposure to 100 micromolar or lower concentrations of Leu-Leu-OMe. With higher concentrations of Leu-Leu-OMe, modest amounts of $^{51}$Cr release and partial loss of proliferative capacity were observed (data not shown). In contrast, a variety of cell types of non-lymphoid, non-myeloid origin including human umbilical vein endothelial cells, the human renal cell carcinoma line, Currie, the human epidermal carcinoma line, HEp-2, and human dermal fibroblasts demonstrated no significant Leu-Leu-OMe induced $^{51}$Cr release. Furthermore, incubation of each of these non-lymphoid cell types with 500 micromolar Leu-Leu-OMe had no discernible effect on subsequent proliferative capacity (data not shown).

HS-Sultan, a human plasma cell line (Goldblum et al. (1973) Proc. Seventh Leucocyte Culture Conference, ed by Daguilland, Acad. Press N.Y. pp 15-28), Daudi, a B lymphoblastoid cell line (Klein et al. (1968) Cancer Res. V 28, p 1300), MoLT-4, an acute lymphoblastic T-cell leukemia line (Monowada et al. (1972) J. Nat'l. Canc. Inst. V 49, p 891), and U-937, a human monocyte-like cell line (Koren et al. (1979) Nature V 279, p 891) were obtained from the American Type Culture Collection, Rockville, Md. These lines as well as HEp-2 a human epidermoid carcinoma line (a generous gift of Dr. R. Sontheimer, UTHSCD); Currie, a human renal cell carcinoma line (a generous gift of Dr. M. Prager, UTHSCD); and K562, a human erythroleukemia line (a generous gift of Dr. M. Bennett, UTHSCD) were maintained in culture in medium RMPI supplemented with 10% FBS. Human dermal fibroblasts (a generous gift of Dr. T. Geppert, UTHSCD) were serially passaged in culture as well while human umbilical vein endothelial cells (a generous gift of Dr. A. Johnson, UTHSCD) were used after one subculture. Epstein Barr virus (EBV) transformed B lymphoblastoid cell lines JM.6 and SM.4 (kindly provided by Dr. J. Moreno, UTHSCD) and cloned EBV transformed B cell lines SDL-G2 and D8-219 (a generous gift of Drs. L. Stein and M. Dosch, Hospital for Sick Children, Toronto, Canada) were maintained in culture in medium RPMI supplemented with 10% FBS.

In some experiments, toxicity of Leu-Leu-OMe for a variety of cell populations was assessed by $^{51}$Cr release. In assays where cells obtained from suspension culture were to be used, cells were labeled with $Na_2{}^{51}CrO_4$ (ICN, Plainview, N.Y.) for 60-90 minutes at 37° C. and then washed three times. Cells were then suspended in PBS ($2.5 \times 10^6$/ml) and incubated in microtiter plates, 50 microL/well with indicated concentrations of Leu-Leu-OMe for 15 minutes at room temperature. In assays where cells were obtained from monolayer cultures, microtiter wells were seeded with cells ($5 \times 10^4$/well) and cultured for 24 hours at 37° C. Cells were then labeled with $Na_2{}^{51}CrO_4$ while in adherent culture. Following $^{51}$Cr labeling, wells were thoroughly washed and varying concentrations of Leu-Leu-OMe added in 50 microL PBS and the plates incubated for 15 minutes at room temperature.

Following such initial serum-free incubations, 200 microL/well of medium RPMI containing 10% FBS were added and the plates incubated for another 4 hours prior to removal of 100 microliters of supernatant. Radioactivity in the supernatant was measured in an auto-gamma scintillation spectrometer (Packard Instrument Co., Downers Grove, Ill.). The percent specific release was calculated from the formula:

$$\% \text{ spec. release } (rel) = \frac{\text{exp. } rel \text{ } (cpm) - \text{spont. } rel \text{ } (cpm)}{\text{max. } rel \text{ } (cpm) - \text{spont. } rel \text{ } (cpm)}$$

in which maximal release refers to cpm obtained in wells containing 50% lysing agent (American Scientific Products, McGraw Park, Ill.) and spontaneous release refers to cpm released by cells incubated in control medium in the absence of Leu-Leu-OMe or the lysing agent. Only experiments in which spontaneous release was 25% were used for subsequent data interpretation.

While the MP-like tumor line U937 was virtually identical to MP in susceptibility to Leu-Leu-OMe, none of the non-lymphoid, non-myeloid cell lines tested demonstrated such susceptibility to Leu-Leu-OMe mediated toxicity.

The current example demonstrates that at concentrations 10 to 20 fold greater than those at which cytotoxic cells are ablated, Leu-Leu-OMe does have some minimal toxicity for certain non-cytotoxic lymphoid cells such as EBV transformed B cells and K562 cells. Yet, while it is impossible to exhaustively exclude the possibility that certain non-cytotoxic cells might also be equally sensitive to Leu-Leu-OMe-mediated toxicity, at present the ability to function as a mediator of cell mediated cytotoxicity is the one unifying characteristic of the cell types which are rapidly killed by exposure to Leu-Leu-OMe.

Figure 7:
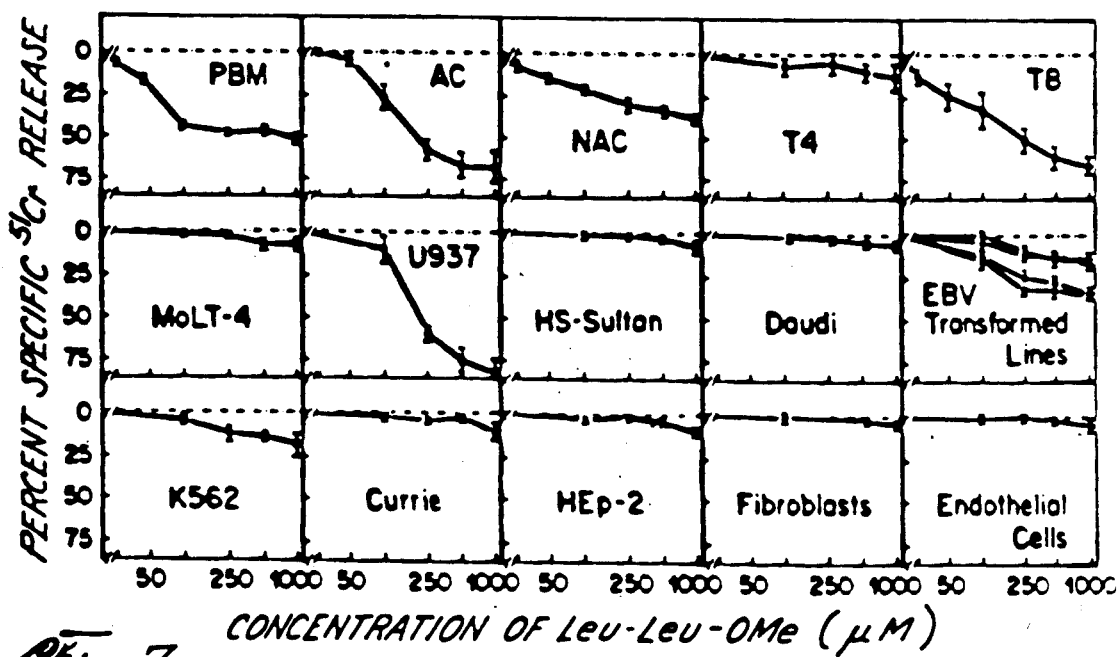
FIG. 7 shows the toxicity of various Leu-Leu-OMe concentrations for selected cell types.

In developing the data expressed in FIG. 7, cells ($2.5 \times 10^6$/ml) were exposed to the indicated concentrations of Leu-Leu-OMe for 15 minutes at room temperature, then specific $^{51}$Cr release during the next four hours was assessed. Data for the EBV transformed lines JM.6, SDL-G2, D8-219, and SM.4, respectively, are shown in order from top to bottom.

EXAMPLE 12

Relative Sensitivity of CTL and NK to Leu-Leu-OMe

Figure 8:
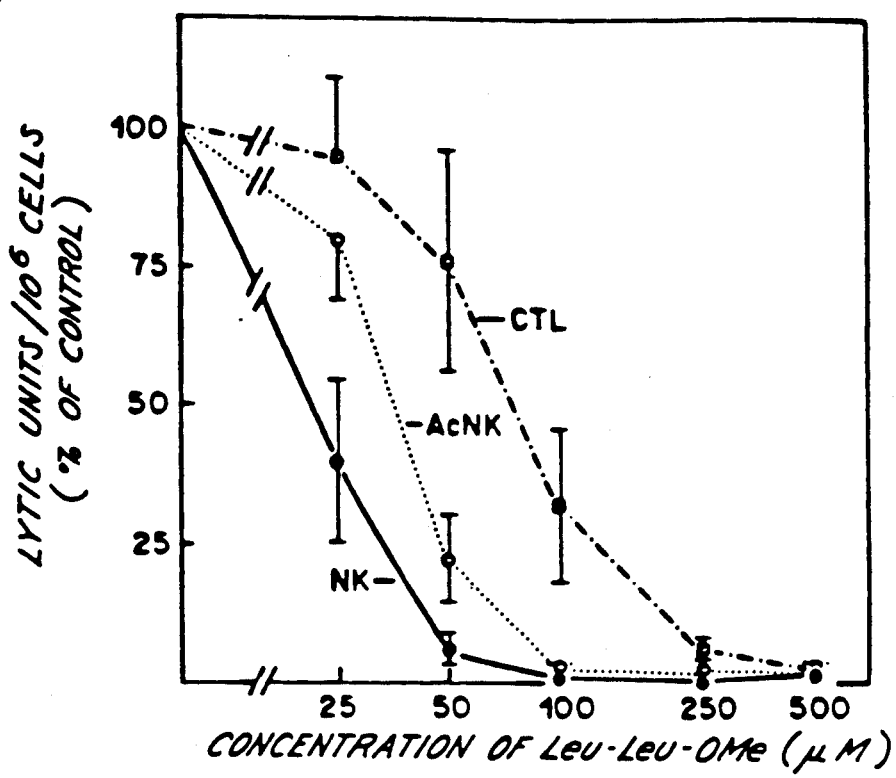
FIG. 8 shows the Leu-Leu-OMe mediated elimination of precursors of cytotoxic T lymphocytes, activated NK ($A_cNK$) and NK.

Experiments were also designed to assess the relative sensitivity of NK and CTL to Leu-Leu-OMe. In the studies detailed in FIG. 8 and 9, cytotoxicity assays were performed over a broad range of E:T ratios and units of lytic activity arising from equal numbers of responding lymphocytes were calculated and compared. As shown in FIG. 8, both spontaneous NK and precursors of activated NK were totally eliminated by exposure to 100 micromolar Leu-Leu-OMe while CTL precursors, though diminished, were generally still present at greater than 50% of control levels. Only after exposure to greater than 250 micromolar Leu-Leu-OMe were all CTL precursors eliminated.

FIG. 8 shows that incubation with Leu-Leu-OMe eliminates precursors of cytotoxic T lymphocytes (CTL) and activated NK-like cells (AcNK). Non-adherent lymphocytes ($2.5 \times 10^6$/ml) were incubated with the indicated concentrations of Leu-Leu-OMe for 15 minutes. Cells were then washed and either placed in mixed lymphocyte culture or assayed for specific lysis of K562 cells (NK). After 6 day MLC, cells were assayed for specific lysis of allogeneic stimulator lymphoblasts (CTL) or K562 (AcNK). Data are expressed as percent of control lytic units (mean +SEM, n=6).

Figure 9:
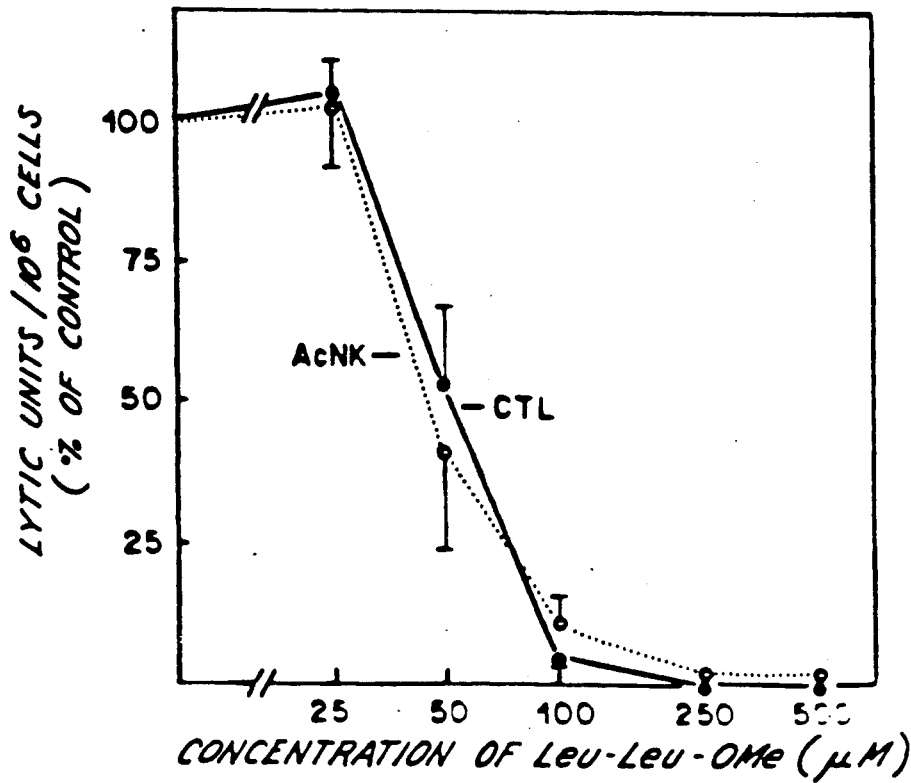
FIG. 9 shows the sensitivity of CTL and AcNK cells to Leu-Leu-OMe following activation.

When the elimination of CTL and activated NK precursors by Leu-Leu-OMe was compared to that of spontaneous NK, the mean Leu-Leu-OMe concentration required to diminish lytic activity by 75% was significantly greater for elimination of CTL precursors ($123 \pm 25$ micromolar) than for elimination of precursors of activated NK ($50 \pm 5$ micromolar, p 0.05). Both values were also higher than the mean concentration of Leu-Leu-OMe required to diminish spontaneous NK lytic activity by 75% (35 micromolar$\pm 4$ micromolar). FIG. 9 shows that, following activation, CTL and AcNK became identical in sensitivity to Leu-Leu-OMe. After 6 day MLC, cells were incubated for 15 minutes with the indicated concentrations of Leu-Leu-OMe, then assayed for CTL or AcNK activity as for FIG. 8. Thus, only after MLC activation did CTL display a sensitivity to Leu-Leu-OMe toxicity that was equal to that of NK cells.

Changes may be made in the construction, operation and arrangement of the various elements, steps and procedures described herein without departing from the concept and scope of the invention as defined in the following claims.

What is claimed is:

1. A method of treating a patient for bone marrow graft versus host disease, comprising the step of contacting bone marrow cells to be grafted into said patient with an alkyl ester of a dipeptide, said alkyl dipeptide ester comprising an amount sufficient to substantially deactivate natural killer cells or cytotoxic T-lymphocytes, said dipeptide alkyl esters consisting essentially of the L-amino acids leucine, phenylalanine, valine, isoleucine, alanine, proline, glycine, or aspartic acid beta-methyl ester, individually or in combination.

2. A method of treating a patient for bone marrow graft versus host disease comprising the step of contacting the bone marrow cells to be grafted into said patient with an alkyl ester of a dipeptide, said dipeptide alkyl ester comprising an amount sufficient to substantially deactivate natural killer cells or cytotoxic T-lymphocytes, said dipeptide alkyl esters consisting essentially of L-amino acids with hydrophobic side chains.

3. The method of claim 2 wherein the dipeptide is L-leucyl L-leucine, L-leucyl L-phenylalanine, L-valyl L-phenylalanine, L-phenylalanyl L-leucine, L-leucyl L-isoleucine, L-phenylalanyl L-phenylalanine, L-valyl L-leucine, L-leucyl L-alanine, L-valyl L-valine, L-prolyl L-leucine, L-leucyl L-valine, L-phenylalanyl L-valine, L-glycyl L-leucine, L-leucyl L-glycine, or l-aspartyl beta methyl ester L-phenylalanine.

4. The method of claim 2 wherein the dipeptide is L-leucyl L-leucine, L-leucyl L-phenylalanine, L-valyl L-phenylalanine, L-phenylalanyl L-leucine, L-leucyl L-isoleucine, L-phenylalanyl L-phenylalanine or L-valyl L-leucine.

5. The method of claim 2 where the amount sufficient to substantially deactivate natural killer cells or cytotoxic T-lymphocytes is between about 25 micromolar and 250 micromolar, said concentrations being achieved by administration of about 100–300 mg/kg body weight.

6. The method of claim 2 wherein the alkyl ester is a methyl ester, ethyl ester, propyl ester, isopropyl ester, butyl ester or isobutyl ester.

* * * * *